(12) United States Patent
Wendland (10) Patent No.: US 11,793,943 B2
(45) Date of Patent: Oct. 24, 2023

(54) NEEDLE ARRANGEMENT

(71) Applicant: Sanofi-Aventis Deutschland GMBH, Frankfurt am Main (DE)

(72) Inventor: Stefan Wendland, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 475 days.

(21) Appl. No.: 16/348,080

(22) PCT Filed: Oct. 30, 2017

(86) PCT No.: PCT/EP2017/077713
§ 371 (c)(1),
(2) Date: May 7, 2019

(87) PCT Pub. No.: WO2018/091256
PCT Pub. Date: May 24, 2018

(65) Prior Publication Data
US 2019/0298936 A1    Oct. 3, 2019

(30) Foreign Application Priority Data

Nov. 15, 2016  (EP) .................................... 16198915

(51) Int. Cl.
*A61M 5/32* (2006.01)
*A61M 5/20* (2006.01)
(Continued)

(52) U.S. Cl.
CPC .......... *A61M 5/329* (2013.01); *A61M 5/2033* (2013.01); *A61M 5/3297* (2013.01);
(Continued)

(58) Field of Classification Search
CPC .......... A61M 2005/2474; A61M 5/329; A61M 5/2033; A61M 2205/0216
See application file for complete search history.

(56) References Cited

U.S. PATENT DOCUMENTS

| 5,613,500 A | * | 3/1997 | Bishop | A61M 5/3232 |
| | | | | 604/110 |
| 6,123,688 A | * | 9/2000 | Botich | A61M 5/24 |
| | | | | 604/203 |

(Continued)

FOREIGN PATENT DOCUMENTS

| CN | 203802884 | 9/2014 |
| JP | 2002-530162 | 9/2002 |

(Continued)

OTHER PUBLICATIONS

PCT International Preliminary Report on Patentability in International Appln. No. PCT/EP2017/077713, dated May 21, 2019, 7 pages.

(Continued)

*Primary Examiner* — Bhisma Mehta
*Assistant Examiner* — John J Crawford
(74) *Attorney, Agent, or Firm* — Fish & Richardson P.C.

(57) ABSTRACT

The present disclosure relates to a needle arrangement for a drug delivery device. The needle arrangement includes a distal needle tip and a proximal needle tip. The distal needle tip is held in a distal needle holder and wherein the proximal needle tip is held in a proximal needle holder. The distal needle tip and the proximal needle tip are in fluid communication with each other through a fluid channel. The fluid channel is adapted to allow axial movement of the distal needle tip and relative to the proximal needle tip between a compact state and an extended state. A length of the needle arrangement over the distal needle tip and the proximal (Continued)

needle tip in the extended state is greater than in the compact state.

17 Claims, 6 Drawing Sheets

(51) Int. Cl.
*A61M 5/24* (2006.01)
*A61M 5/28* (2006.01)
(52) U.S. Cl.
CPC ........... *A61M 5/288* (2013.01); *A61M 5/3287* (2013.01); *A61M 2005/2474* (2013.01); *A61M 2205/0216* (2013.01)

(56) References Cited

U.S. PATENT DOCUMENTS

| | | | |
|---|---|---|---|
| 6,605,067 B1 * | 8/2003 | Larsen | A61M 5/3287 604/192 |
| 2014/0180218 A1 * | 6/2014 | Fourt | A61M 5/2033 604/220 |
| 2015/0208974 A1 * | 7/2015 | Teoh | A61M 5/178 600/577 |
| 2015/0217089 A1 | 8/2015 | Chuang et al. | |
| 2016/0324455 A1 * | 11/2016 | Crosby | A61B 5/150244 |
| 2017/0106135 A1 * | 4/2017 | Bengtsson | A61M 5/001 |

FOREIGN PATENT DOCUMENTS

| | | |
|---|---|---|
| JP | 2017-510365 | 4/2017 |
| WO | WO 2000/030705 | 6/2000 |
| WO | WO 2015/150179 | 10/2015 |

OTHER PUBLICATIONS

PCT International Search Report and Written Opinion in International Appln. No. PCT/EP2017/077713, dated Jan. 22, 2018, 10 pages.

* cited by examiner

NEEDLE ARRANGEMENT

CROSS REFERENCE TO RELATED APPLICATIONS

The present application is the national stage entry of International Patent Application No. PCT/EP2017/077713, filed on Oct. 30, 2017, and claims priority to Application No. EP 16198915.7, filed on Nov. 15, 2016, the disclosures of which are incorporated herein by reference.

TECHNICAL FIELD

The disclosure generally relates to a needle arrangement for a drug delivery device.

BACKGROUND

Needle arrangements having a distal needle tip for piercing an injection site and a proximal needle tip for piercing a septum of a medicament cartridge are known in the art.

There remains a need for an improved needle arrangement.

SUMMARY

In some aspects, a needle assembly is provided.

According to the present disclosure, a needle arrangement for a drug delivery device comprises a distal needle tip and a proximal needle tip, wherein the distal tip is held in a distal needle holder and wherein the proximal tip is held in a proximal needle holder, wherein the distal needle tip and the proximal needle tip are in fluid communication with each other through a fluid channel, wherein the fluid channel is adapted to allow axial movement of the distal needle tip and relative to the proximal needle tip between a compact state and an extended state, wherein a length of the needle arrangement over the distal needle tip and the proximal needle tip in the extended state is greater than in the compact state.

This allows for a needle arrangement with a variable length so that the drug delivery device, in which the needle arrangement is to be applied, can be made shorter than required with a conventional fixed length needle assembly.

In an exemplary embodiment the distal needle tip and the proximal needle tip are telescoped one within the other thus creating the fluid channel.

In an exemplary embodiment the fluid channel is flexible.

In an exemplary embodiment a spring is arranged between the distal needle holder and the proximal needle holder biasing the needle arrangement towards the expanded state. This allows for keeping the needle arrangement in the compact state until use and releasing the proximal needle holder so that the proximal needle tip pierces the septum driven by the spring.

In an exemplary embodiment the spring is adapted to act in two directions, e.g. to pierce a medicament cartridge and to pierce an injection site, e.g. a skin of a patient.

In an exemplary embodiment the spring is formed by the flexible fluid channel. This reduces the part count and hence costs and resource consumption.

In an exemplary embodiment the flexible fluid channel is formed as a helical spring.

In an exemplary embodiment the flexible fluid channel is formed as an S-shaped spring.

In an exemplary embodiment the flexible fluid channel is arranged within an expandable elastomer body which may be is arranged as a gaiter or bellows. The expandable elastomer body may serve as a support for the spring.

In an exemplary embodiment, the flexible fluid channel is arranged as an elastic tube.

In an exemplary embodiment, at least one of the needle holders and/or the expandable elastomer body has a guiding surface adapted to be guided by corresponding surfaces within a drug delivery device.

In an exemplary embodiment, the guiding surface is cylindrical.

In an exemplary embodiment, the distal needle tip and the proximal needle tip point in opposite directions.

In an exemplary embodiment, the needle assembly may not comprise a spring.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
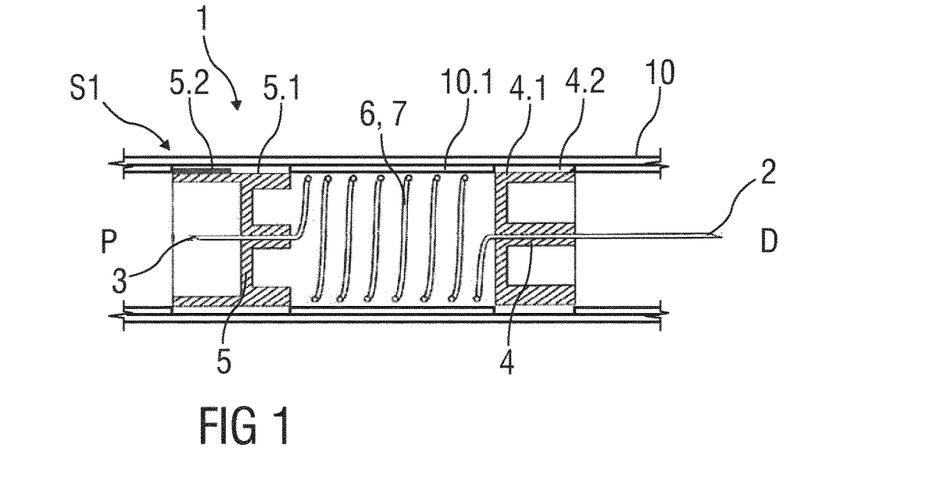
FIG. 1 is a schematic view of an exemplary first embodiment of a needle arrangement in a compact state.

FIG. 1 is a schematic view of an exemplary first embodiment of a needle arrangement 1 in a compact state S1. The needle arrangement 1 comprises a distal needle tip 2 and a proximal needle tip 3 pointing in opposite directions, wherein the distal needle tip 2 is held in a distal needle holder 4 and wherein the proximal tip 3 is held in a proximal needle holder 5. The distal needle tip 2 and the proximal needle tip 3 are in fluid communication with each other through a flexible fluid channel 6. In the illustrated embodiment, the flexible fluid channel 6 is arranged as a spring 7, in particular a helical spring and integrally formed with the distal needle tip 2 and the proximal needle tip 3, i.e. the distal needle tip 2 forms one end of the helical spring 7 and the proximal needle tip 3 forms another end of the helical spring 7.

In an exemplary embodiment, the distal needle tip 2 is adapted to be inserted into an injection site, e.g. a patient's skin and the proximal needle tip 3 is adapted to pierce a septum of a medicament cartridge (not illustrated).

The needle arrangement 1 may be assembled into a drug delivery device adapted to receive a medicament cartridge.

Figure 2:
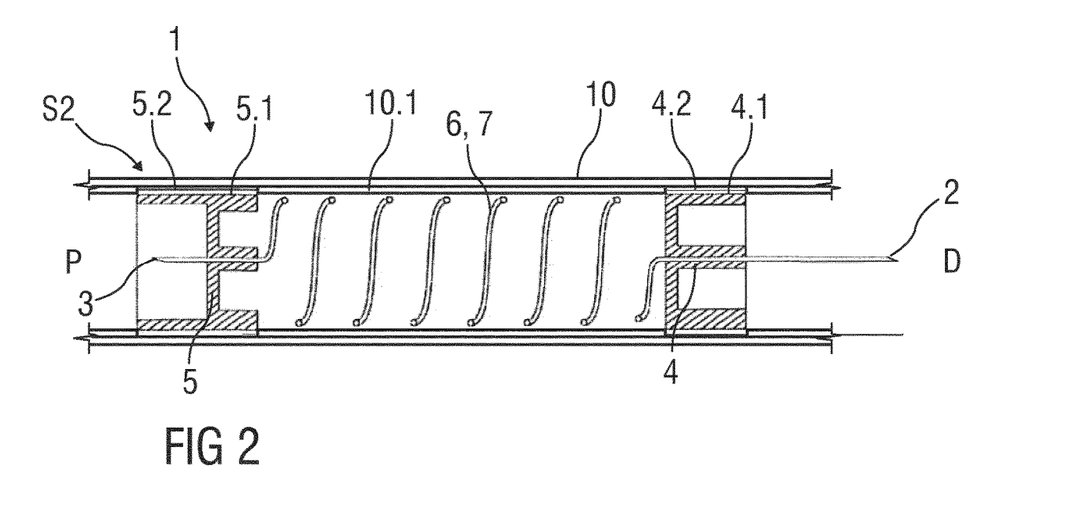
FIG. 2 is a schematic view of the first embodiment of the needle arrangement in an extended state.

In an exemplary embodiment, the distal needle holder 4 and the proximal needle holder 5 may have guide ribs 4.2, 5.2 and/or grooves to facilitate assembling and to guide the needle arrangement 1 within the drug delivery device so that the needle holders 4 and 5 move in parallel relative to each other. In the illustrated embodiment, guide ribs 4.2, 5.2 are arranged on the distal needle holder 4.2 and the proximal needle holder 5.2, the guide ribs 4.2, 5.2 adapted to engage a groove 10.1 within a drug delivery device 10. In an exemplary embodiment, the groove 10.1 may be arranged in a tubular body part of the drug delivery device 10. In another exemplary embodiment, the groove 10.1 may be arranged in the distal needle holder 4.2 and the proximal needle holder 5.2 while the drug delivery device 10 may have one or more corresponding guide ribs 4.2, 5.2. Alternatively, a separate guiding element may be provided to guide the needle arrangement 1 within the drug delivery device 10 so that the needle holders 4 and 5 move in parallel relative to each other. When the needle arrangement 1 is assembled into the drug delivery device, the needle assembly 1 is in the compact state S1, i.e. the helical spring 7 forming the flexible fluid channel 6 is compressed as shown in FIG. 1 and the needle tips 2 and 3 are thus biased against each other. The needle holders 4 and 5 have guiding surfaces 4.1, 5.1, which may for example be cylindrical. These guiding surfaces 4.1, 5.1 are adapted to be guided by corresponding surfaces within a drug delivery device, e.g. a cartridge holder and/or a needle sleeve. In an exemplary embodiment, when the drug delivery device is activated, e.g. by removing a cap, operating a trigger button, pushing a skin contact sleeve, pulling or twisting a lever, the proximal needle holder 5 is released and due to the energy stored in the helical spring 7 advances the proximal needle tip 3 away from the distal needle tip 2 in a proximal direction P towards the medicament cartridge to pierce the septum and to arrive in an extended state S2 as shown in FIG. 2. The drug delivery device may now be in a condition in which an injection site may be pierced. In an optional further step, the distal needle holder 4 may be released to advance the distal needle tip 2 away from the proximal needle tip 3 in a distal direction D to pierce the injection site. The distal needle holder 4 may be locked in this state in order to prevent the distal needle tip 2 from retracting when being pushed against the injection site.

The spring 7 may be adapted to act in two directions to pierce the medicament cartridge and to pierce the injection site, e.g. a skin of a patient. In an alternative embodiment, there may be two springs 7, one of them acting in a first direction to pierce the medicament cartridge and the other one acting in a second direction to pierce the injection site.

Figure 3:
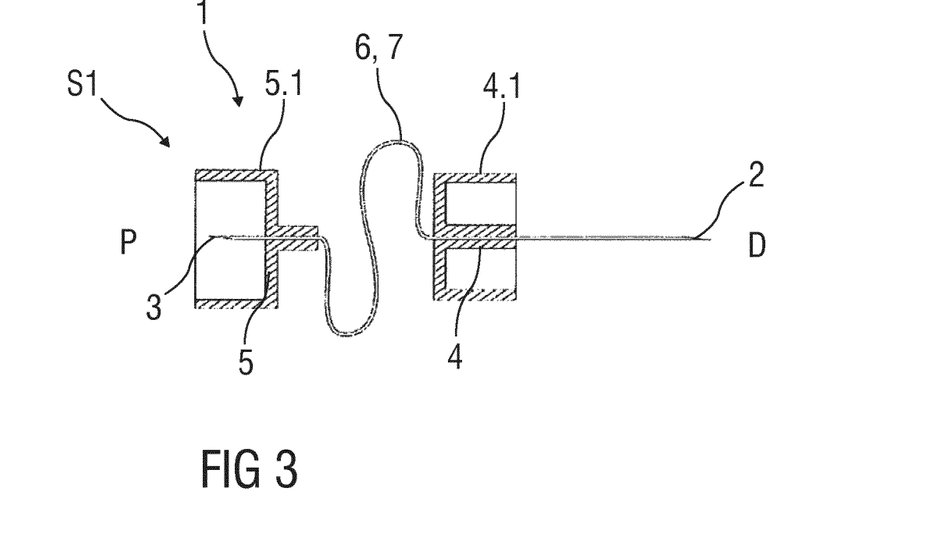
FIG. 3 is a schematic view of an exemplary second embodiment of a needle arrangement in a compact state.

FIG. 3 is a schematic view of an exemplary second embodiment of a needle arrangement 1 in a compact state S1. The needle arrangement 1 comprises a distal needle tip 2 and a proximal needle tip 3 pointing in opposite directions, wherein the distal needle tip 2 is held in a distal needle holder 4 and wherein the proximal tip 3 is held in a proximal needle holder 5. The distal needle tip 2 and the proximal needle tip 3 are in fluid communication with each other through a flexible fluid channel 6. In the illustrated embodiment, the flexible fluid channel 6 is arranged as a spring 7, in particular an S-shaped spring, and integrally formed with the distal needle tip 2 and the proximal needle tip 3, i.e. the distal needle tip 2 forms one end of the S-shaped spring 7 and the proximal needle tip 3 forms another end of the S-shaped spring 7.

In an exemplary embodiment, the distal needle tip 2 is adapted to be inserted into an injection site, e.g. a patient's skin and the proximal needle tip 3 is adapted to pierce a septum of a medicament cartridge (not illustrated).

The needle arrangement 1 may be assembled into a drug delivery device adapted to receive a medicament cartridge.

Figure 4:
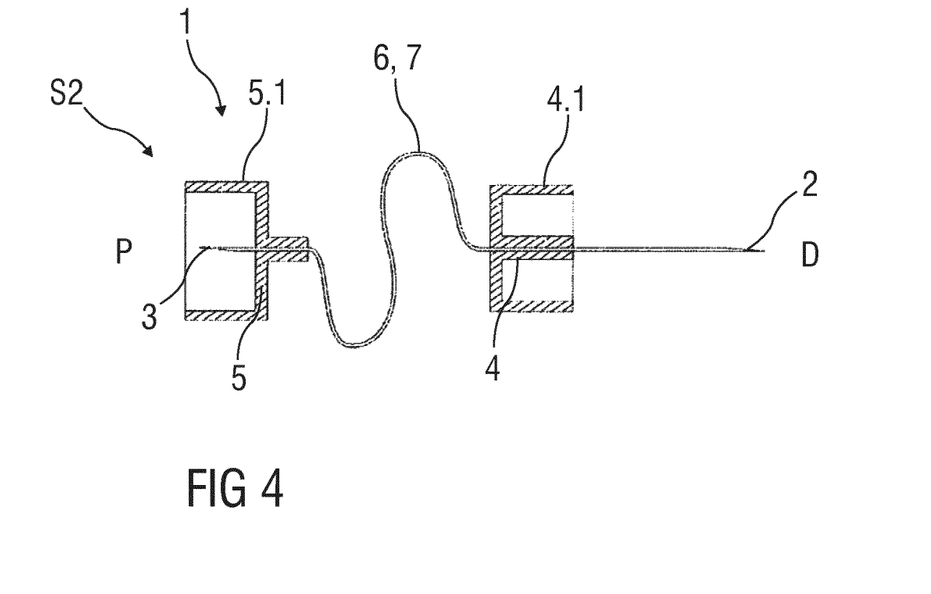
FIG. 4 is a schematic view of the second embodiment of the needle arrangement in an extended state.

In an exemplary embodiment, the distal needle holder 4 and the proximal needle holder 5 may have guide grooves and/or ribs to facilitate assembling and to guide the needle arrangement 1 within the drug delivery device. When the needle arrangement 1 is assembled into the drug delivery device, the needle assembly 1 is in the compact state S1, i.e. the S-shaped spring 7 forming the flexible fluid channel 6 is compressed as shown in FIG. 3 and the needle tips 2 and 3 are thus biased against each other. The needle holders 4 and 5 have guiding surfaces 4.1, 5.1, which may for example be cylindrical. These guiding surfaces 4.1, 5.1 are adapted to be guided by corresponding surfaces within a drug delivery device, e.g. a cartridge holder and/or a needle sleeve. In an exemplary embodiment, when the drug delivery device is activated, e.g. by removing a cap, the proximal needle holder 5 is released and due to the energy stored in the S-shaped spring 7 advances the proximal needle tip 3 away from the distal needle tip 2 in a proximal direction P towards the medicament cartridge to pierce the septum and to arrive in an extended state S2 as shown in FIG. 4. In an optional further step, the distal needle holder 4 may be released to advance the distal needle tip 2 away from the proximal needle tip 3 in a distal direction D to pierce the injection site. The distal needle holder 4 may be locked in this state in order to prevent the distal needle tip 2 from retracting when being pushed against the injection site.

Figure 5:
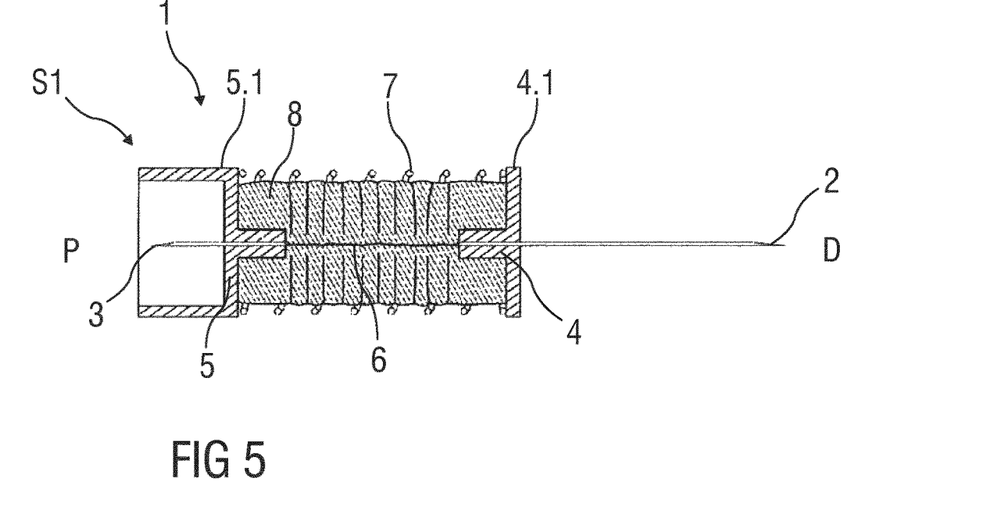
FIG. 5 is a schematic view of an exemplary third embodiment of a needle arrangement in a compact state.

FIG. 5 is a schematic view of an exemplary third embodiment of a needle arrangement 1 in a compact state S1. The needle arrangement 1 comprises a distal needle tip 2 and a proximal needle tip 3 pointing in opposite directions, wherein the distal needle tip 2 is held in a distal needle holder 4 and wherein the proximal tip 3 is held in a proximal needle holder 5. The distal needle tip 2 and the proximal needle tip 3 are in fluid communication with each other through a flexible fluid channel 6. In the illustrated embodiment, the flexible fluid channel 6 is arranged within an expandable elastomer body 8, which may be arranged as a gaiter or bellows. A spring 7, in particular a helical spring, may be arranged about the expandable elastomer body 8. The elastomer body 8 may serve as a support for the spring 7.

In an exemplary embodiment, the distal needle tip 2 is adapted to be inserted into an injection site, e.g. a patient's skin and the proximal needle tip 3 is adapted to pierce a septum of a medicament cartridge (not illustrated).

The needle arrangement 1 may be assembled into a drug delivery device adapted to receive a medicament cartridge.

Figure 6:
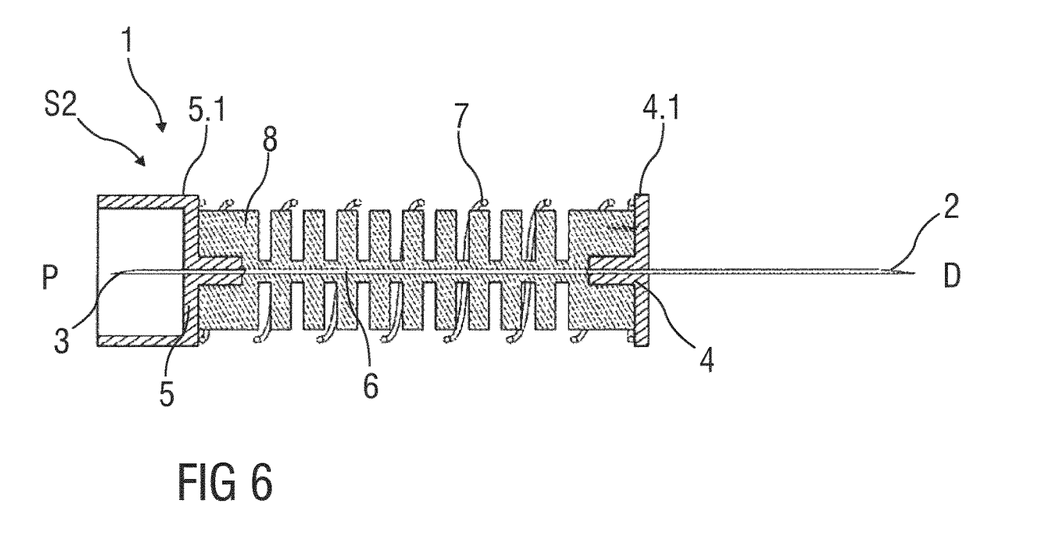
FIG. 6 is a schematic view of the third embodiment of the needle arrangement in an extended state.

In an exemplary embodiment, the distal needle holder 4 and the proximal needle holder 5 may have guide grooves and/or ribs to facilitate assembling and to guide the needle arrangement 1 within the drug delivery device. When the needle arrangement 1 is assembled into the drug delivery device, the needle assembly 1 is in the compact state S1, i.e. the needle holders 4 and 5 are pushed towards each other and the expandable elastomer body 8 and the spring 7 are compressed as shown in FIG. 5 and the needle tips 2 and 3 are thus biased against each other. In an exemplary embodiment, the needle holders 4 and/or 5 may have guiding surfaces 4.1, 5.1, which may for example be cylindrical. In another embodiment, at least the distal needle holder 4 does not have a guiding surface 4.1 but is guided by the expandable elastomer body 8. The guiding surfaces 4.1 and/or 5.1 and/or the expandable elastomer body 8 are adapted to be guided by corresponding surfaces within a drug delivery device, e.g. a cartridge holder and/or a needle sleeve. In an exemplary embodiment, when the drug delivery device is activated, e.g. by removing a cap, the proximal needle holder 5 is released and due to the energy stored in the spring 7 advances the proximal needle tip 3 away from the distal needle tip 2 in a proximal direction P towards the medicament cartridge to pierce the septum and to arrive in an extended state S2 as shown in FIG. 6. In an optional further step, the distal needle holder 4 may be released to advance the distal needle tip 2 away from the proximal needle tip 3 in a distal direction D to pierce the injection site. The distal needle holder 4 may be locked in this state in order to prevent the distal needle tip 2 from retracting when being pushed against the injection site.

Figure 7:
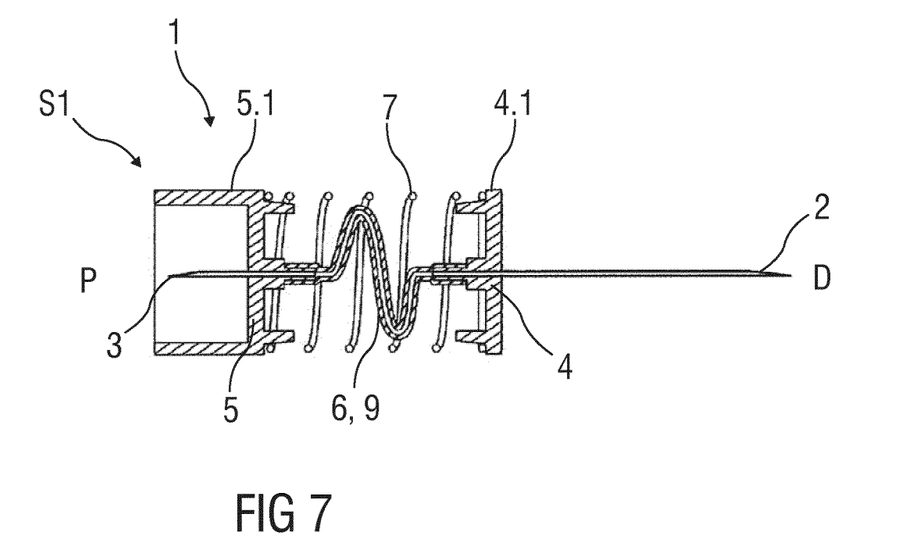
FIG. 7 is a schematic view of an exemplary fourth embodiment of a needle arrangement in a compact state.

FIG. 7 is a schematic view of an exemplary fourth embodiment of a needle arrangement 1 in a compact state S1. The needle arrangement 1 comprises a distal needle tip 2 and a proximal needle tip 3 pointing in opposite directions, wherein the distal needle tip 2 is held in a distal needle holder 4 and wherein the proximal tip 3 is held in a proximal needle holder 5. The distal needle tip 2 and the proximal needle tip 3 are in fluid communication with each other through a flexible fluid channel 6. In the illustrated embodiment, the flexible fluid channel 6 is arranged as an elastic tube 9. A spring 7, in particular a helical spring, may be arranged about the flexible fluid channel 6.

In an exemplary embodiment, the distal needle tip 2 is adapted to be inserted into an injection site, e.g. a patient's skin and the proximal needle tip 3 is adapted to pierce a septum of a medicament cartridge (not illustrated).

The needle arrangement 1 may be assembled into a drug delivery device adapted to receive a medicament cartridge.

Figure 8:
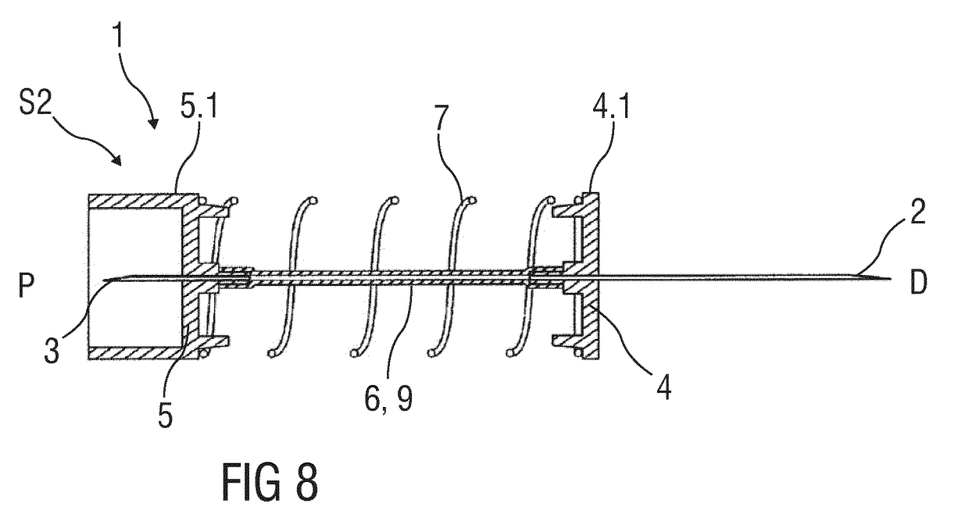
FIG. 8 is a schematic view of the fourth embodiment of the needle arrangement in an extended state.

In an exemplary embodiment, the distal needle holder 4 and the proximal needle holder 5 may have guide grooves and/or ribs to facilitate assembling and to guide the needle arrangement 1 within the drug delivery device. When the needle arrangement 1 is assembled into the drug delivery device, the needle assembly 1 is in the compact state S1, i.e. the spring 7 is compressed as shown in FIG. 7, the needle tips 2 and 3 are thus biased against each other and the flexible fluid channel 6 is slack. The needle holders 4 and 5 have guiding surfaces 4.1, 5.1, which may for example be cylindrical. These guiding surfaces 4.1, 5.1 are adapted to be guided by corresponding surfaces within a drug delivery device, e.g. a cartridge holder and/or a needle sleeve. In an exemplary embodiment, when the drug delivery device is activated, e.g. by removing a cap, the proximal needle holder 5 is released and due to the energy stored in the spring 7 advances the proximal needle tip 3 away from the distal needle tip 2 in a proximal direction P towards the medicament cartridge to pierce the septum and to arrive in an extended state S2 as shown in FIG. 8. In the extended state S2 the flexible fluid channel 6 may be tight. In an optional further step, the distal needle holder 4 may be released to advance the distal needle tip 2 away from the proximal needle tip 3 in a distal direction D to pierce the injection site. The distal needle holder 4 may be locked in this state in order to prevent the distal needle tip 2 from retracting when being pushed against the injection site. In this case, the flexible fluid channel 6 may not yet be tight in the extended state S2 prior to release of the distal needle holder 4.

Figure 9:
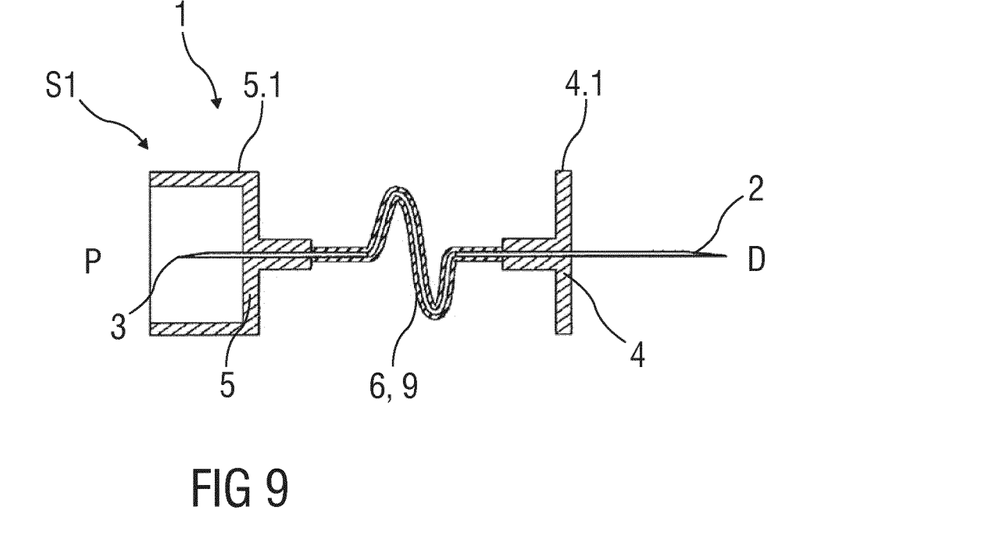
FIG. 9 is a schematic view of an exemplary fifth embodiment of a needle arrangement in a compact state.

FIG. 9 is a schematic view of an exemplary fifth embodiment of a needle arrangement 1 in a compact state S1. The needle arrangement 1 comprises a distal needle tip 2 and a proximal needle tip 3 pointing in opposite directions, wherein the distal needle tip 2 is held in a distal needle holder 4 and wherein the proximal tip 3 is held in a proximal needle holder 5. The distal needle tip 2 and the proximal needle tip 3 are in fluid communication with each other through a flexible fluid channel 6. In the illustrated embodiment, the flexible fluid channel 6 is arranged as an elastic tube 9. In the fifth embodiment, the needle arrangement 1 does not comprise a spring.

In an exemplary embodiment, the distal needle tip 2 is adapted to be inserted into an injection site, e.g. a patient's skin and the proximal needle tip 3 is adapted to pierce a septum of a medicament cartridge (not illustrated).

The needle arrangement 1 may be assembled into a drug delivery device adapted to receive a medicament cartridge.

Figure 10:
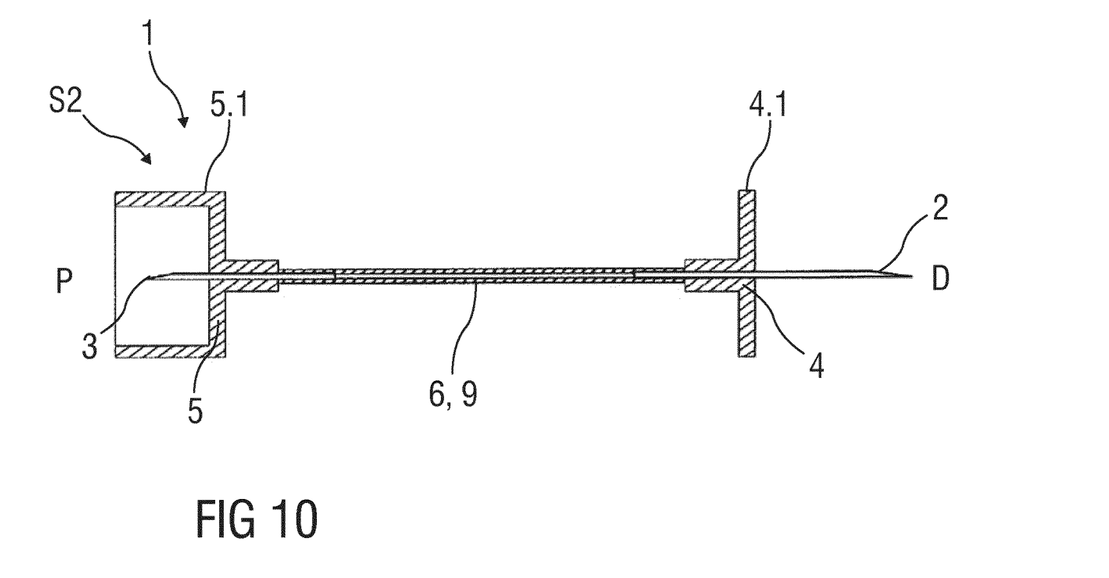
FIG. 10 is a schematic view of the fifth embodiment of the needle arrangement in an extended state.

In an exemplary embodiment, the distal needle holder 4 and the proximal needle holder 5 may have guide grooves and/or ribs to facilitate assembling and to guide the needle arrangement 1 within the drug delivery device. When the needle arrangement 1 is assembled into the drug delivery device, the needle assembly 1 is in the compact state S1, i.e. the needle tips 2 and 3 are moved towards each other and the flexible fluid channel 6 is slack as shown in FIG. 9. The needle holders 4 and 5 have guiding surfaces 4.1, 5.1, which may for example be cylindrical. These guiding surfaces 4.1, 5.1 are adapted to be guided by corresponding surfaces within a drug delivery device, e.g. a cartridge holder and/or a needle sleeve. In an exemplary embodiment, when the drug delivery device is activated, e.g. by removing a cap, the proximal needle holder 5 is advanced by a mechanism of the drug delivery device away from the distal needle tip 2 in a proximal direction P towards the medicament cartridge to allow the proximal needle tip 3 to pierce the septum and to arrive in an extended state S2 as shown in FIG. 10. In the extended state S2 the flexible fluid channel 6 may be tight. In an optional further step, the distal needle holder 4 may be advanced by a mechanism of the drug delivery device to advance the distal needle tip 2 away from the proximal needle tip 3 in a distal direction D to pierce the injection site. The distal needle holder 4 may be locked in this state in order to prevent the distal needle tip 2 from retracting when being pushed against the injection site. In this case, the flexible fluid channel 6 may not yet be tight in the extended state S2 prior to release of the distal needle holder 4.

Figure 11:
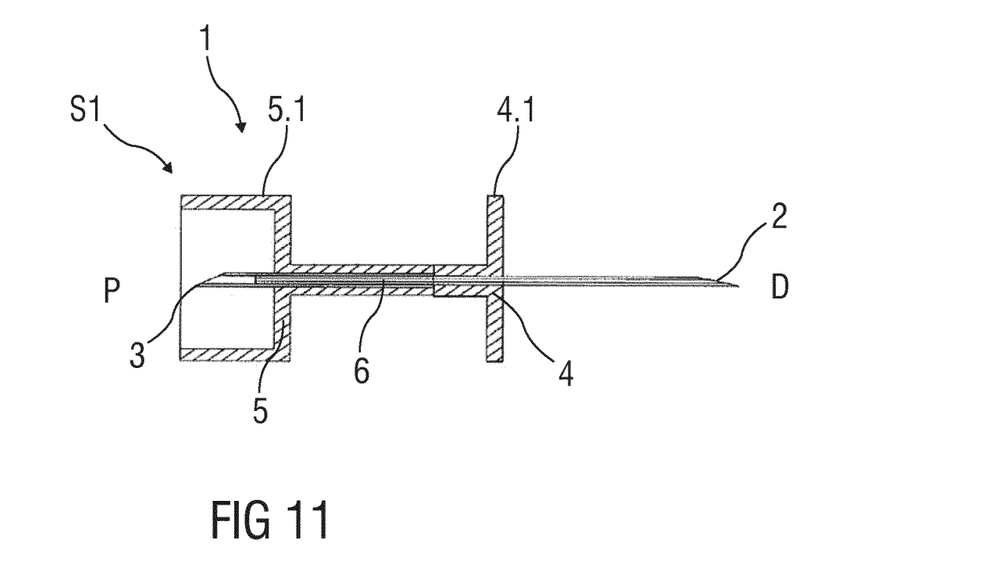
FIG. 11 is a schematic view of an exemplary sixth embodiment of a needle arrangement in a compact state.

FIG. 11 is a schematic view of an exemplary sixth embodiment of a needle arrangement 1 in a compact state S1. The needle arrangement 1 comprises a distal needle tip 2 and a proximal needle tip 3 pointing in opposite directions, wherein the distal needle tip 2 is held in a distal needle holder 4 and wherein the proximal tip 3 is held in a proximal needle holder 5. The distal needle tip 2 and the proximal needle tip 3 are telescoped one within the other thus creating a fluid channel 6 for establishing a fluid communication with each other. In the sixth embodiment, the needle arrangement 1 does not comprise a spring.

In an exemplary embodiment, the distal needle tip 2 is adapted to be inserted into an injection site, e.g. a patient's skin and the proximal needle tip 3 is adapted to pierce a septum of a medicament cartridge (not illustrated).

The needle arrangement 1 may be assembled into a drug delivery device adapted to receive a medicament cartridge.

Figure 12:
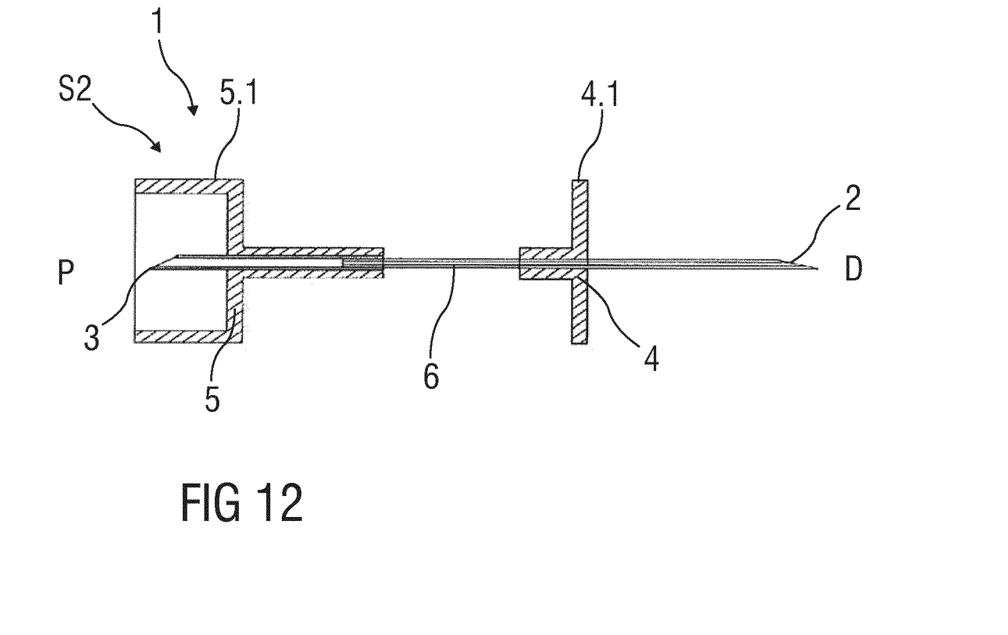
FIG. 12 is a schematic view of the sixth embodiment of the needle arrangement in an extended state.

In an exemplary embodiment, the distal needle holder 4 and the proximal needle holder 5 may have guide grooves and/or ribs to facilitate assembling and to guide the needle arrangement 1 within the drug delivery device. When the needle arrangement 1 is assembled into the drug delivery device, the needle assembly 1 is in the compact state S1, i.e. the needle tips 2 and 3 are moved towards each other as shown in FIG. 11. The needle holders 4 and 5 have guiding surfaces 4.1, 5.1, which may for example be cylindrical. These guiding surfaces 4.1, 5.1 are adapted to be guided by corresponding surfaces within a drug delivery device, e.g. a cartridge holder and/or a needle sleeve. In an exemplary embodiment, when the drug delivery device is activated, e.g. by removing a cap, the proximal needle holder 5 is advanced by a mechanism of the drug delivery device away from the distal needle tip 2 in a proximal direction P towards the medicament cartridge to allow the proximal needle tip 3 to pierce the septum and to arrive in an extended state S2 as shown in FIG. 12. In an optional further step, the distal needle holder 4 may be advanced by a mechanism of the drug delivery device to advance the distal needle tip 2 away from the proximal needle tip 3 in a distal direction D to pierce the injection site. The distal needle holder 4 may be locked in this state in order to prevent the distal needle tip 2 from retracting when being pushed against the injection site.

The telescoped needle tips 2, 3 may be sealed against each other by an exact fit, by a sealing compound and/or by a tube, e.g. a shrink tube.

The sixth embodiment may be modified by adding a spring 7 as in the embodiments of FIGS. 5 to 8.

The guide ribs 4.2, 5.2 and the groove 10.1 of the embodiment of FIGS. 1 and 2 may also be applied in all other embodiments described above.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoylgamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB -1023, TTP-054, Langlenatide/HM-11260C, CM-3, GLP-1 Eligen, ORMD-0901, NN-9924, NN -9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 needle arrangement
2 distal needle tip
3 proximal needle tip
4 distal needle holder
4.1 guiding surface
5 proximal needle holder 5.1 guiding surface
6 fluid channel
7 spring
8 expandable elastomer body
9 elastic tube
10 drug delivery device
D distal direction
P proximal direction
S1 compact state
S2 extended state

The invention claimed is:

1. A needle arrangement for a drug delivery device, the needle arrangement comprising:
   a distal needle tip adapted to be inserted into an injection site; and
   a proximal needle tip adapted to pierce a septum of a medicament cartridge,
   wherein the distal needle tip is configured to be held in a distal needle holder and the proximal needle tip is configured to be held in a proximal needle holder,
   wherein the distal needle tip and the proximal needle tip are in fluid communication with each other through a fluid channel,
   wherein the fluid channel is configured to allow axial movement of the distal needle tip relative to the proximal needle tip between a compact state and an extended state,
   wherein a length of the needle arrangement along the distal needle tip and the proximal needle tip in the extended state is greater than in the compact state,
   wherein one of the distal needle tip and the proximal needle tip is telescoped within the other one of the distal needle tip and the proximal needle tip to create the fluid channel, wherein at least one of the distal needle tip and the proximal needle tip is telescopically movable relative to the other, wherein the distal needle tip and the proximal needle tip point in opposite directions, and wherein a spring is arranged between the distal needle holder and the proximal needle holder biasing the needle arrangement towards the extended state.

2. The needle arrangement according to claim 1, wherein the spring is adapted to act in two directions.

3. The needle arrangement according to claim 1, wherein the fluid channel is arranged within an expandable elastomer body.

4. The needle arrangement according to claim 3, wherein the expandable elastomer body comprises bellows extending between the proximal needle tip and the distal needle tip.

5. The needle arrangement according to claim 3, wherein at least one of the distal needle holder, the proximal needle holder, or the expandable elastomer body has a guiding surface adapted to be guided by corresponding surfaces within the drug delivery device.

6. The needle arrangement according to claim 5, wherein the guiding surface is cylindrical.

7. The needle arrangement according to claim 1, wherein the distal needle tip is telescopically movable relative to the proximal needle tip.

8. The needle arrangement according to claim 1, wherein the proximal needle tip is telescopically movable relative to the distal needle tip.

9. A drug delivery device comprising:
   a distal needle holder;
   a proximal needle holder; and
   a needle arrangement comprising a distal needle tip and a proximal needle tip, wherein the distal needle tip is held in the distal needle holder and wherein the proximal needle tip is held in the proximal needle holder,
   wherein the distal needle tip and the proximal needle tip are in fluid communication with each other through a fluid channel,
   wherein the fluid channel is adapted to allow axial movement of the distal needle tip relative to the proximal needle tip between a compact state and an extended state,
   wherein a length of the needle arrangement along the distal needle tip and the proximal needle tip in the extended state is greater than in the compact state, and
   wherein one of the distal needle tip and the proximal needle tip is telescoped within the other one of the distal needle tip and the proximal needle tip to create the fluid channel, wherein at least one of the distal needle tip and the proximal needle tip is telescopically movable relative to the other, wherein the distal needle tip is adapted to be inserted into an injection site and the proximal needle tip is arranged to pierce a septum of a medicament cartridge, wherein the distal needle tip and the proximal needle tip point in opposite directions, and wherein a spring is arranged between the distal needle holder and the proximal needle holder biasing the needle arrangement towards the extended state.

10. The drug delivery device according to claim 9, wherein the spring is adapted to act in two directions.

11. The drug delivery device according to claim 9, wherein the fluid channel is arranged within an expandable elastomer body.

12. The drug delivery device according to claim 11, wherein the expandable elastomer body comprises bellows extending between the proximal needle tip and the distal needle tip.

13. The drug delivery device according to claim 11, wherein at least one of the distal needle holder, the proximal needle holder, or the expandable elastomer body has a guiding surface adapted to be guided by corresponding surfaces within the drug delivery device, wherein the guiding surface is cylindrical.

14. The drug delivery device according to claim 9, wherein the distal needle tip is telescopically movable relative to the proximal needle tip.

15. The drug delivery device according to claim 9, wherein the proximal needle tip is telescopically movable relative to the distal needle tip.

16. The drug delivery device according to claim 9, wherein the medicament cartridge contains a medicament.

17. A drug delivery device comprising:
   a distal needle holder;
   a proximal needle holder; and
   a needle arrangement comprising a distal needle tip and a proximal needle tip, wherein the distal needle tip is held in the distal needle holder and wherein the proximal needle tip is held in the proximal needle holder,
   wherein the distal needle tip and the proximal needle tip are in fluid communication with each other through a fluid channel,
   wherein the fluid channel is adapted to allow axial movement of the distal needle tip relative to the proximal needle tip between a compact state and an extended state,
   wherein a length of the needle arrangement along the distal needle tip and the proximal needle tip in the extended state is greater than in the compact state, and wherein one of the distal needle tip and the proximal needle tip is telescoped within the other one of the distal needle tip and the proximal needle tip to create the fluid channel,
wherein at least one of the distal needle tip and the proximal needle tip is telescopically movable relative to the other, wherein the distal needle tip is adapted to be inserted into an injection site and the proximal needle tip is arranged to pierce a septum of a medicament cartridge,
wherein the distal needle tip and the proximal needle tip point in opposite directions, and
wherein the proximal needle tip telescopically moves relatively to the distal needle tip in order to pierce the septum of the medicament cartridge.

\* \* \* \* \*